(12) United States Patent
Fleischmann

(10) Patent No.: US 6,863,022 B2
(45) Date of Patent: Mar. 8, 2005

(54) METHOD AND DEVICE FOR REARING INSECTS, ESPECIALLY FOR OBTAINING SECRETION FROM FLY LARVAE FOR THERAPEUTIC APPLICATION

(76) Inventor: Wilhelm Fleischmann, Wieselweg 26, 74321 Bietigheim-Bissingen (DE)

( * ) Notice: Subject to any disclaimer, the term of this patent is extended or adjusted under 35 U.S.C. 154(b) by 0 days.

(21) Appl. No.: 10/384,843

(22) Filed: Mar. 10, 2003

(65) Prior Publication Data

US 2003/0172875 A1 Sep. 18, 2003

Related U.S. Application Data

(62) Division of application No. 09/762,575, filed as application No. PCT/EP00/05132 on Jun. 6, 2002, now Pat. No. 6,557,487.

(30) Foreign Application Priority Data

Jun. 8, 1999 (DE) .......................................... 199 25 996

(51) Int. Cl.$^7$ .............................................. A01K 29/00
(52) U.S. Cl. ........................................ 119/6.6; 119/6.5
(58) Field of Search ........................... 119/311, 6.5, 6.6; 424/537

(56) References Cited

U.S. PATENT DOCUMENTS

| | | | | | |
|---|---|---|---|---|---|
| 4,368,690 | A | * | 1/1983 | Tenzer | 119/6.6 |
| 4,417,545 | A | * | 11/1983 | Finney | 119/6.6 |
| 4,646,683 | A | * | 3/1987 | Maedgen, Jr. | 119/6.5 |
| 4,726,471 | A | * | 2/1988 | Whately et al. | 206/554 |
| 4,765,275 | A | * | 8/1988 | Yukawa et al. | 119/6.7 |
| 4,988,019 | A | * | 1/1991 | Dawes | 99/287 |
| 5,351,643 | A | * | 10/1994 | Hughes | 119/6.5 |

FOREIGN PATENT DOCUMENTS

| | | | | |
|---|---|---|---|---|
| CN | 1142887 A | | 2/1997 | ......... A01K/67/033 |
| CN | 1213497 | | 4/1999 | ......... A01K/67/033 |
| GB | 2124864 A | * | 2/1984 | ......... A01K/97/02 |
| GB | 2229991 A | * | 10/1990 | ......... B65D/33/14 |
| WO | WO 92/11760 A1 | | 1/1992 | ......... A01N/1/02 |
| WO | WO 95/26633 A1 | | 3/1995 | ......... A01N/59/04 |
| WO | PCT/IB00/00592 | * | 5/2000 | ......... A61L/15/18 |

* cited by examiner

Primary Examiner—Teri P. Luu
Assistant Examiner—Kimberly S. Smith
(74) Attorney, Agent, or Firm—Pendorf & Cutliff

(57) ABSTRACT

The invention relates to a device for breeding of insects for therapeutic application of secretions of fly larvae (maggots) on a wound. The device includes an application container for receiving the fly eggs. The fly larvae from the egg stage up to the maggot stage is develop inside the application container and the maggots are grown until they secrete a therapeutically active secretion. The application container is maintain under development conditions influenced in a controlled manner which retard the further development of the eggs for storage. The application container includes fluid transmissive walls that allow the passing of secretions produced by the maggot through the walls of the application container into the wound but prevents passage of the maggots enclosed in the application container. In addition, the device of the present invention includes an incubation container to maintain the eggs in controlled incubating conditions. The conditions for retarding the further development of the eggs includes at least one of cooling, dehumidification, evacuation, an inert gas atmosphere, and chemical or biochemical retardants, individually or in combination.

13 Claims, 2 Drawing Sheets

METHOD AND DEVICE FOR REARING INSECTS, ESPECIALLY FOR OBTAINING SECRETION FROM FLY LARVAE FOR THERAPEUTIC APPLICATION

CROSS REFERENCE TO RELATED APPLICATION

This application is Divisional of Ser. No. 09/762,575 FILED Feb. 8, 2001 now U.S. Pat. No. 6,557,487, entitled "METHOD AND DEVICE FOR REARING INSECTS, ESPECIALLY FOR OBTAINING SECRETION FROM FLY LARVAE FOR THERAPEUTIC APPLICATION", allowed Dec. 13, 2002, which is a national stage of PCT/EP00/05132 filed Jun. 6, 2002 and based upon DE 199 25 996.8 filed Jun. 8, 1999 under the International Convention.

BACKGROUND OF THE INVENTION

1. Field of the Invention

Process and device for rearing of insects, in particular for obtaining the secretions of fly larvae for therapeutic application.

2. Description of the Related Art

The invention concerns a process and a device for rearing insects, in particular for obtaining the secretions of fly larvae (maggots) for therapeutic application.

For treatment of wound infections and wounds, which contain necrotized tissue, for example for treatment of diabetic gangrene, fly larvae, so-called maggots, are employed, in particular larvae of Diptera from the family Muscidae, Sarcophaginae and Calliphoridae (for example, Lucilia, Blue Bottle). The larvae are introduced for a certain amount of time, for example, approximately three days, into a wound for which it is difficult to render therapy. It has been shown that the larvae within this time removed necrotized tissue in the wound, eliminated bacterial infections, and stimulated wound healing. This effect is in particular brought about by the digestive secretions excreted by the maggots. This secretion fluidizes the necrotized tissue, so that it can be ingested by the maggots as nutrition. The secretion further has a strongly bactericidal effect and promotes wound healing.

In this method of treatment it is necessary to have living maggots available which can be applied to the wound so that they secrete the healing secretions. This brings about, for the employment of this method, a substantial logistical problem, since the period of time of the active maggot stage, in which the healing secretions are secreted, is relatively short and has a duration-of only a few days. It is necessary that the maggots be transported from the producer, who breeds the maggots, to the user immediately prior to application. This necessitates an exactly coordinated plan. Besides this, the maggots are relatively sensitive and must be provided with air and nutrients during transport. On the basis of these difficulties, the employment of the fly larvae therapy is limited in its possibilities and full advantage cannot be taken thereof.

SUMMARY OF THE INVENTION

The invention is based on the task of providing a process and a device through which the breeding of insects can occur in a controlled manner, and in particular, through which the therapeutic application of fly larvae secretion is simplified and facilitated.

BRIEF DESCRIPTION OF THE DRAWINGS

The invention is described in greater detail in the following figures.

DETAILED DESCRIPTION OF THE INVENTION

Figure 1:
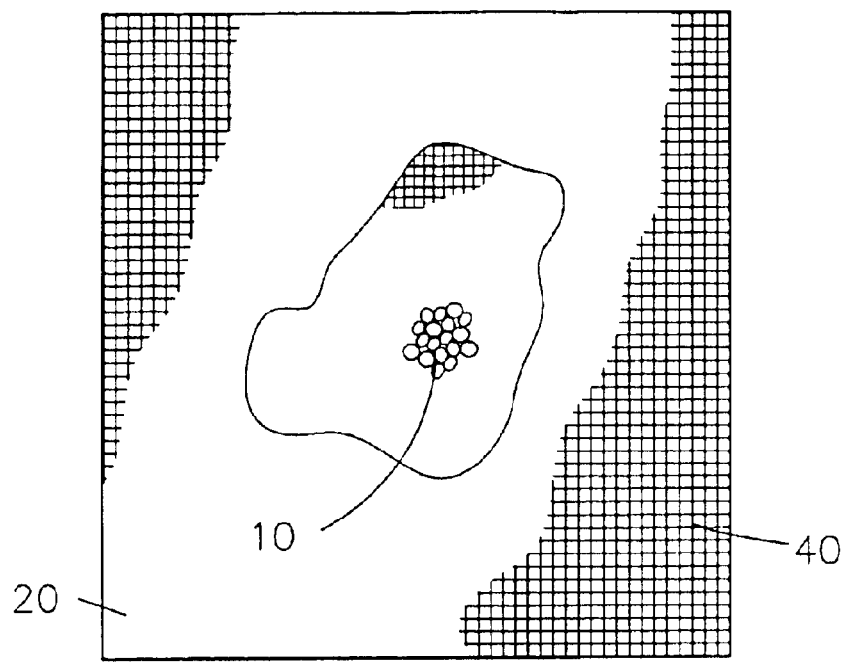
FIG. 1 shows an application container having the wall broken away to show the eggs.
Figure 2:
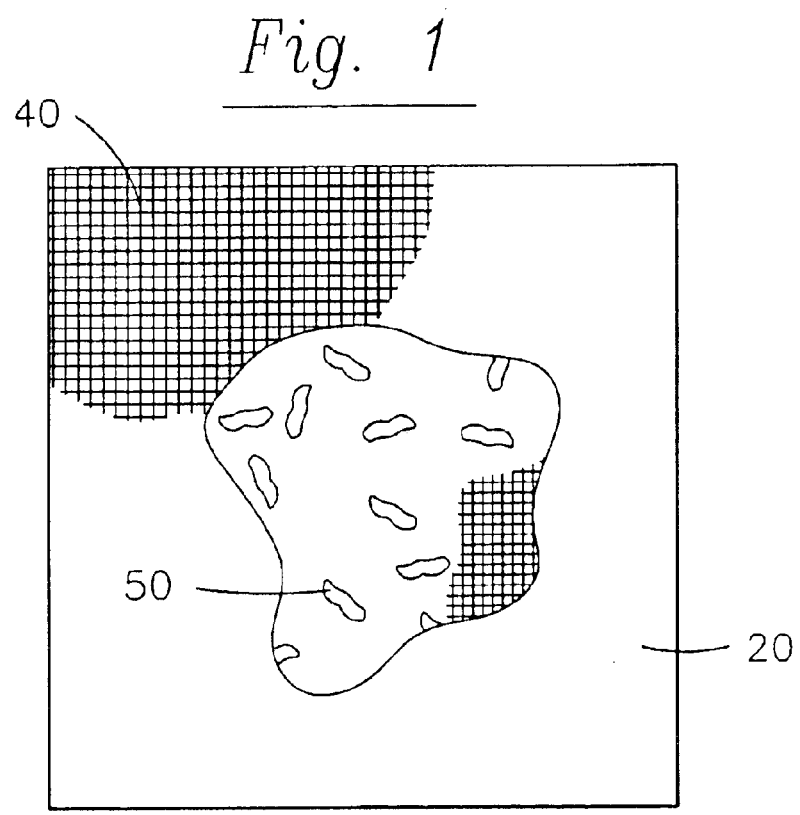
FIG. 2 shows an application container having the wall broken away to show the maggots.
Figure 3:
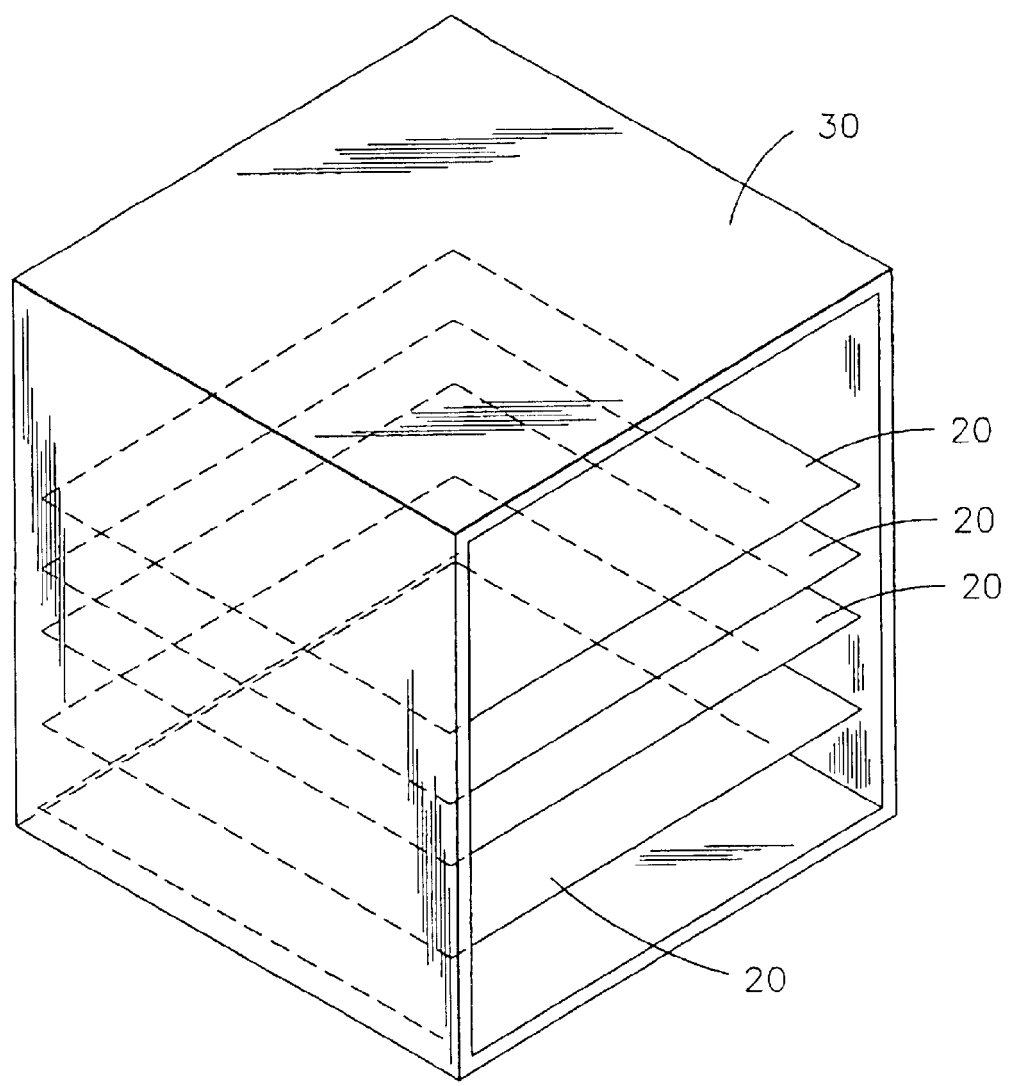
FIG. 3 shows the inside of an incubation container having inside several application containers.

The essential idea of the invention is comprised therein, that the breeding of the insects is to be carried out in an enclosed biotope under exactly defined environmental conditions, as a result of which the development cycle can be intentionally influenced. Thereby it is made possible to study the development and the behavior of the insects under targeted, varied physical, chemical, biochemical, and biological conditions and to influence the conditions for the medical-therapeutic and pharmaceutical use. Thereby, the speed of the development cycle can be influenced by changing the conditions, that is, it can be delayed or accelerated. Besides this, it becomes possible by targeted, influenced measures to raise the quality and the yield.

In the utilization of the process for obtaining the secretion of fly larvae for therapeutic application, one essential aspect is comprised in arresting the development of the fly larvae in the egg stage and to store and/or to transport these eggs under development retarding conditions. At the manufacturer, who breeds the flies, the fly eggs are separated and preferably disinfected so that they are sufficiently sterile. The sterilized eggs are enclosed in a self-enclosed biotope, for example a container, in which the further development of the eggs is carried out or maintained under restrictive or retarding conditions. Such conditions could include that the eggs are cooled and/or stored in a dehumidified atmosphere. Further, the eggs can be stored in an oxygen-poor atmosphere, in which the container is, for example, evacuated or filled with an inert gas. Further possible are reversible chemical/biochemical influences (for example Neb-TMOF), which results in oostasis for a defined period of time. These measures can be employed individually or in combination. These resilient and tolerant eggs can be kept alive for prolonged periods of time under these restrictive development conditions. This makes it possible for the producer to store the eggs for a certain period of time. Further, the eggs can be transported to the user in simple manner under these conditions, without risk of damage. It is further possible for the end user to maintain a certain supply of eggs, for example in a clinic, for a certain period of time, so that the respective actual needs can be satisfied.

If the maggot secretion is to be applied, then the user reactivates the further development of the eggs into the larval stage. For this, the development retarding conditions are lifted and the eggs are subjected to incubating conditions, so that they further develop and within a short period of time hatch into maggots. Since the eggs are sterilized at the producer, the hatched maggots are also sterile and can be employed without problem.

It is also possible to culture microorganisms in the artificially produced microbiologically-closed living environment, in order to heighten or to change the effect of the maggots and their microbiologically modified secretions.

The maggots can be introduced immediately into the wound in the known manner, and after a certain treatment time must again be removed from the wound. In one variation, the maggots are introduced in the wound in an application container. One such application container includes a fluid transmissive wall, which however does not allow passage of the maggots enclosed in the application container. For example, the application container can be a flexible bag with a net-like wall. The secretion secreted by the maggots can pass through the wall of the application container and into the wound. The wound tissue fluidized by the secretion can likewise pass through the wall of the application container and be taken up by the maggots. An application container of this type has the advantage, that the maggots and therewith the secretions secreted by these maggots can be applied in targeted, localized manner. Besides this, maggots can be removed from the wound in simple manner, together with the application container.

Finally, it is also possible to bring the maggots into contact with a porous wound insert, which absorbs the secretions secreted by the maggots. In this case, the wound insert soaked with the secretion is applied to the wound. This has the advantage, that the wound insert can be applied temporally and spatially separate from the maggots, which simplifies the application and avoids the problem of the occasional patient refusing treatment with living maggots.

Preferably the incubation of the eggs 10 up to the hatching of the maggots 50 occurs in an incubation container 30. The eggs are introduced in this incubation container 30 and incubated at a temperature of between 20 and 40° C. The incubation container 30 is provided with sufficient nutrient substances and air for the hatching larvae, so that these can develop up to the larval stage, at which they secrete the therapeutic secretions. This incubation container is preferably produced as a bag comprised of plastic foil and preferably includes an absorbent material for absorbing the produced active substances under sterile or microbiologically controlled conditions.

In a preferred embodiment, the eggs 10 can be enclosed in an application container 20 and introduced into the incubation container 30. These small eggs 10 are kept in the application container 20 by the incubation container 30, so that they do not fall out of this net-like wall. When the larvae hatch out of the eggs, they can take up the nutrient substances from out of the incubation container and grow in the application container to the size at which they secrete the therapeutically active secretions. At this size, they can no longer slip out of the net-like wall of the application container. The application container can then be removed from the incubation container, or as the case may be, the incubation container can be moved from the application container, so that the maggots can be applied to the wound directly with the application container, or can be brought into contact with a porous wound insert.

In an embodiment particularly simple for the user, the eggs are introduced into the incubation container already by the producer and initially maintained at development retarding conditions for storage and transport. For this, the incubation containers are evacuated, or filled with a dried inert gas, or are chemically/biochemically oostatically manipulated. Likewise, or in certain cases additionally, the incubation containers can be placed in a cooling container and cooled for storage and transport.

When the maggots are to be applied, incubation conditions are established in the incubation containers. For this, the incubation containers, together with the eggs, are introduced into a warm environment. The incubation containers are supplied with oxygen-containing air, the nutrients necessary for the hatching larvae, and in certain cases, activating chemical or biochemical factors (for example peptidases). For administration of oxygen, the wall of the incubation container can be punctured with a canula, or an opening can be provided. As appropriate, it is also possible to introduce the necessary nutrients and, in certain cases, to introduce the oostatic influencing deactivating substances into the incubation container in this manner. In a variation particularly convenient for the user, it is possible that air, nutrient solutions, and other substances are provided in the incubation container during the manufacture thereof in enclosed containers or enclosed ampullae's, which can be disrupted by the user, so that air and nutrient solutions, as well as in certain cases chemical, biochemical, and microbiological components, are released into the incubation containers, which promotes hatching and which can be taken up by the hatched maggots.

If the flies are transported to the user in the egg stage, so that the maggots are hatched by the user for the application of the secretion, then as a rule, the maggots are terminated as soon as they are removed from the wound, or after they have secreted the secretion onto the wound insert.

At the producer, preferably utilizing a component of the population of the insects, the complete development cycle is carried out in a time-wise modifiable and controllable biotope. After the hatching of the maggots, these are in certain cases used for obtaining the secretion, which then is made available for the user in the a form suitable for application, or for manufacture of pharmaceutical preparations. At the end of the larvae stage, the conditions necessary for pupating are then established in the biotope, for example drying air conditions.

The maggots then pupate so that a new generation of insects hatches, which can then again be used for depositing of eggs under sterile conditions. The raising of the insects from egg up to hatched fly under time-wise, manipulable and controllable conditions provides the producer with the possibility to match the time and yield of the production of the maggots, or as the case may be, the maggot secretions, to the market requirements. Besides this, the insect populations can be bred and influenced, in order to achieve an increase in productivity and quality. Finally, a targeted microbiological influence on the closed development biotope is possible, so that a therapeutic synergistic effect can be achieved, for example by the select supplementation of bacteria to the secretions secreted by the maggots.

What is claimed is:

1. A device for breeding insects for therapeutic application of secretions of fly larvae on a wound comprising:
   a closed application container enclosing fly eggs,
   means for maintaining the application container under controlled first conditions to retard the development of the eggs for storage;
   means for maintaining the application container under controlled second conditions to develop the fly eggs into fly larvae until they secrete a therapeutically active secretion; and
   wherein the application container includes fluid transmissive walls that allows the passing of the secretions produced by the fly larvae through the walls of the application container into the wound but prevents passage of the fly larvae enclosed in the application container.

2. A device according to claim 1 wherein the first controlled conditions include at least one of cooling, dehumidification, evacuation, an inert gas atmosphere, and chemical or biochemical retardants, individually or in combination.

3. A device according to claim 1 wherein the application container includes a flexible net-like wall.

4. A device according to claim 1 further including a porous wound insert to absorb the secretion secreted by the maggots and apply the secretion to the wound.

5. A device according to claim 1 wherein the means for maintaining the application container under first controlled conditions is chosen from cooling, dehumidification, evacuation under an inert gas atmosphere, use of chemical or biochemical retardants, or combination thereof.

6. A device for breeding insects for therapeutic application of secretions of fly larvae on a wound, the device comprising:

a closed incubation container;

a closed application container enclosing fly eggs, wherein the application container is located inside the incubation container, means for maintaining the incubation container under a first controlled condition to retard the development of the eggs for storage and transportation; and means for maintaining the incubation container under a controlled second condition to develop the fly eggs into the fly larvae until they secrete a therapeutically active secretion;

wherein the incubation container includes at least one of air, nutrients, chemical components, biochemical components, microbiological components for hatching the fly larvae;

wherein the application container includes fluid transmissive walls that allows the passing of the secretions produced by the fly larvae through the walls of the application container into the wound but prevents passage of the fly larvae enclosed in the application container; and wherein the application container is applied directly into the wound.

7. A device according to claim 6, wherein the incubation container is a plastic foil container.

8. A device according to claim 6, wherein the incubation container further includes two or more application containers.

9. A device according to claim 6, wherein the first controlled conditions are convertible to the second controlled conditions.

10. A device according to claim 6 wherein at least one of air, nutrients, chemical components, biochemical components, and microbiological components are supplied through a wall of the incubation container.

11. A device according to claim 10, wherein the at least one of air, nutrients, chemical components, biochemical components, and microbiological components are supplied through a wall of the incubation container by using a canula.

12. A device for breeding insects for therapeutic application of secretions of fly larvae on a wound comprising:

a closed application container enclosing fly eggs, at least one of cooling device, dehumidification device, evacuation device under an inert gas atmosphere, chemical or biochemical retardants, or combination thereof to maintain the application container under controlled first conditions to retard the development of the eggs for storage;

at least one of air supply device, nutrients supply device, chemical components supply device, biochemical components supply device, microbiological components supply device, or combination thereof to maintain the application container under controlled second conditions to develop the fly eggs into fly larvae until they secrete a therapeutically active secretion, wherein the application container includes fluid transmissive walls that allows the passing of the secretions produced by the fly larvae through the walls of the application container into the wound but prevents passage of the fly larvae enclosed in the application container.

13. A device for breeding insects for therapeutic application of secretions of fly larvae on a wound, the device comprising:

a closed incubation container;

a closed application container enclosing fly eggs, wherein the application container is located inside the incubation container, at least one of cooling device, dehumidification device, evacuation device under an inert gas atmosphere, chemical or biochemical retardants, or combination thereof to maintain the incubation container under controlled first conditions to retard the development of the eggs for storage;

at least one of air supply device, nutrients supply device, chemical components supply device, biochemical components supply device, microbiological components supply device, or combination thereof to maintain the incubation container under controlled second conditions to develop the fly eggs into fly larvae until they secrete a therapeutically active secretion, wherein the application container includes fluid transmissive walls that allows the passing of the secretions produced by the fly larvae through the walls of the application container into the wound but prevents passage of the fly larvae enclosed in the application container; and wherein the application container is applied directly into the wound.

* * * * *